United States Patent [19]
Azbel

[11] Patent Number: 5,767,415
[45] Date of Patent: Jun. 16, 1998

[54] METHOD FOR NON-DESTRUCTIVE DETERMINATION OF FATIGUE LIMITS AND FRACTURE TOUGHNESS IN COMPONENTS OF VARIOUS SHAPES

[76] Inventor: Vladimir Azbel, Tsizling ST. 15/13, Beer-Sheva, Israel

[21] Appl. No.: 670,388

[22] Filed: Jun. 25, 1996

[51] Int. Cl.[6] .............................. G01N 3/22; G01N 3/26
[52] U.S. Cl. .................... 73/847; 73/794; 73/814
[58] Field of Search ........................... 73/760, 805, 806, 73/808, 814, 794, 795, 847

[56] References Cited

U.S. PATENT DOCUMENTS

| | | | |
|---|---|---|---|
| 3,911,734 | 10/1975 | Mehdizadeh | 73/801 |
| 4,567,774 | 2/1986 | Manahan et al. | 73/808 |
| 5,022,273 | 6/1991 | Evans | 73/849 |
| 5,152,172 | 10/1992 | Leon et al. | 73/579 |
| 5,156,053 | 10/1992 | Shiraishi et al. | 73/849 |
| 5,531,122 | 7/1996 | Chatham et al. | 73/806 |

FOREIGN PATENT DOCUMENTS

| | | |
|---|---|---|
| 567996 | 8/1977 | U.S.S.R. |
| 1587400 | 8/1990 | U.S.S.R. |

Primary Examiner—George M. Dombroske
Assistant Examiner—Max H. Noori
Attorney, Agent, or Firm—Mark M. Friedman

[57] ABSTRACT

A method for non-destructive determination of a fatigue limit for a component includes two sub-methods which may be performed separately, or in any order. A direct-deformation sub-method includes measuring micro-plastic deformation corresponding to each of a plurality of different known values of stress applied to the component, and identifying a critical value of stress corresponding to a change in the relationship between stress and micro-plastic deformation. An internal-friction damping method includes initiating torsional oscillations in the component, measuring an initial angular amplitude of oscillation, $A_o$, and a final angular amplitude of oscillation, $A_n$, at the end of the number, n, of oscillations. This process is repeated a number of times and, for each pair of measurements, a corresponding measure of damping is calculated. A critical value of initial angular amplitude corresponding to a change in the relationship between amplitude and damping is then calculated. All testing is preferably performed torsionally, thereby making the method applicable to a wide range of real components of different shapes. Applied stresses are limited to below the yield point of the materials tested and do not affect the properties of the material.

12 Claims, 5 Drawing Sheets

1

METHOD FOR NON-DESTRUCTIVE DETERMINATION OF FATIGUE LIMITS AND FRACTURE TOUGHNESS IN COMPONENTS OF VARIOUS SHAPES

FIELD AND BACKGROUND OF THE INVENTION

The present invention relates to testing of materials and, in particular, it concerns an apparatus and method for non-destructive determination of fatigue limits in components of various shapes.

It is known that mechanical components subjected to repeated loading are at risk of rupture due to fatigue failure. In order to prevent costly and potentially dangerous accidents, the design of mechanical systems must take into consideration the fatigue properties of the materials employed.

Conventional methods for testing fatigue properties of materials involve repeated loading of multiple samples of the material. Each sample is subjected to a particular level of repeated loading and the number of loading cycles before rupture occurs is counted. This type of testing generally requires about fifteen samples, several of which are tested for in the order of $10^7$–$10^8$ cycles. The entire testing procedure typically takes a couple of weeks to complete. It is clearly impossible to employ this method for testing the condition of real components since the samples are destroyed during testing.

Soviet Patent No. 1,587,400 to Lavrovich discloses a laboratory technique for non-destructive measurement of a fatigue limit of a material. The technique employs cyclic tensile loading of a specimen of the material with the load being increased by steps. For each value of load, a relative dissipation energy is calculated. A point of inflection in the characteristic of energy dissipation plotted against load is used to estimate an endurance limit.

Although Lavrovich correctly identifies a link between the phenomenon of a fatigue limit and the energy dissipation of a material, he fails to present an operative method or apparatus for evaluating fatigue limits for real materials. Specifically, the tensile testing described will only yield the required results for monocrystaline specimens. In standard polycrystaline materials, the complex response of the material under tensile stress completely masks the point of inflection.

Soviet Patent Application No. 75/567,996 to Ermolin et al. discloses a method of testing turbine blades for the effects of overheating. The method includes exciting bending vibration in the blade at its resonant frequency and two adjacent frequencies, and calculating a measure of internal friction. A decrease of 10% from a previously measured value is indicative of deterioration due to overheating.

The method of Ermolin et al. employs an arbitrary fixed criterion for identifying deterioration without taking into consideration the specific properties of the materials involved. Furthermore, the method fails to provide any quantitative information relating to a fatigue limit of the material tested. Additionally, the use of bending vibration precludes the application of the method of Ermolin et al. to components of complex shapes.

There is therefore a need for a non-destructive method of determining fatigue limits applicable to components of a variety of shapes. It would also be advantageous to provide an apparatus for measuring fatigue limits in a wide variety of real components.

SUMMARY OF THE INVENTION

The present invention is of an apparatus and method for non-destructive determination a fatigue limit for a component.

According to the teachings of the present invention there is provided, a non-destructive method of determining a fatigue limit for a component, the method comprising the steps of: (a) measuring a micro-plastic deformation corresponding to each of a plurality of different known values of stress applied to the component; and (b) identifying a critical value of stress corresponding to a change in the relationship between stress and micro-plastic deformation.

According to a further feature of the present invention, the stress is torsional stress.

According to a further feature of the present invention, the fatigue limit of interest is the flexural fatigue limit, the method further comprising a step of multiplying the critical value of stress by a torsional-to-flexural conversion coefficient.

According to a further feature of the present invention, there is also provided a step of applying to the component an environmental condition likely to affect the fatigue limit during the step of measuring.

According to a further feature of the present invention, the environmental condition includes exposure to an elevated temperature.

According to a further feature of the present invention, there are also provided the steps of: (a) initiating torsional oscillations in the component; (b) measuring an initial angular amplitude of oscillation, $A_0$; (c) counting a number, n, of oscillations after measurement of the initial angular amplitude; (d) measuring a final angular amplitude of oscillation, $A_n$ at the end of the number, n, of oscillations; (e) repeating at least steps (c) and (d) a plurality of times for different initial angular amplitudes to obtain a plurality of pairs of measurements $A_0$, $A_n$; (f) for each of the pairs of measurements, calculating a measure of damping corresponding to the initial angular amplitude; and (g) identifying a critical value of initial angular amplitude corresponding to a change in the relationship between amplitude and damping.

There is also provided, according to the teachings of the present invention, a non-destructive method of determining a fatigue limit for a component, the method comprising the steps of: (a) initiating torsional oscillations in the component; (b) measuring an initial angular amplitude of oscillation, $A_0$; (c) counting a number, n, of oscillations after measurement of the initial angular amplitude; (d) measuring a final angular amplitude of oscillation, $A_n$ at the end of the number, n, of oscillations; (e) repeating at least steps (c) and (d) a plurality of times for different initial angular amplitudes to obtain a plurality of pairs of measurements $A_0$, $A_n$; (f) for each of the pairs of measurements, calculating a measure of damping corresponding to the initial angular amplitude; and (g) identifying a critical value of initial angular amplitude corresponding to a change in the relationship between amplitude and damping.

According to a further feature of the present invention, the oscillations are at a frequency of between about 1 and 100 Hz.

According to a further feature of the present invention, the fatigue limit of interest is the flexural fatigue limit, the method further comprising a step of multiplying the critical value of stress by a torsional-to-flexural conversion coefficient.

According to a further feature of the present invention, there is also provided a step of applying to the component an environmental condition likely to affect the fatigue limit during making of the measurements.

According to a further feature of the present invention, the environmental condition includes exposure to an elevated temperature.

According to a further feature of the present invention, there are also provided the steps of: (a) measuring a micro-plastic deformation corresponding to each of a plurality of different known values of stress applied to the component; and (b) identifying a critical value of stress corresponding to a change in the relationship between stress and micro-plastic deformation.

There is also provided, according to the teachings of the present invention, a non-destructive method of deriving information relating to fracture toughness for a component, the method comprising the steps of: (a) initiating torsional oscillations in the component; (b) measuring an initial angular amplitude of oscillation, $A_0$; (c) counting a number, n, of oscillations after measurement of the initial angular amplitude; (d) measuring a final angular amplitude of oscillation, $A_n$ at the end of the number, n, of oscillations; (e) repeating at least steps (c) and (d) a plurality of times for different initial angular amplitudes to obtain a plurality of pairs of measurements $A_0$, $A_n$; (f) for each of the pairs of measurements, calculating a measure of damping corresponding to the initial angular amplitude; and (g) calculating at least one rate of change in the relationship between amplitude and damping.

According to a further feature of the present invention, there is also provided a step of identifying first and second critical points corresponding to changes in the relationship between amplitude and damping, and wherein one of the rates of change is calculated from measurements falling between the first and second critical points.

There is also provided, according to the teachings of the present invention, an apparatus for non-destructive determination of a fatigue limit for a component having a first peripheral part and a second peripheral part substantially opposite to the first peripheral part, the apparatus comprising: (a) a fixed grip for gripping the first peripheral part; (b) a micro-measurement system attached to the second peripheral part, the micromeasurement system including: (i) a torque loading device for applying different values of torque to the component between the first and second peripheral parts, and (ii) a measurement device for making precise measurements of residual angular micro-plastic deformation corresponding to each of the different values of torque applied to the component; and (c) a processor for processing the values of torque and the corresponding angular micro-plastic deformations to identify a critical value of torque corresponding to a change in the relationship between torque and angular deformation.

According to a further feature of the present invention, there is also provided a heating system for substantially enclosing the component, the heating system maintaining the component within a given range of temperatures.

There is also provided, according to the teachings of the present invention, an apparatus for non-destructive determination of a fatigue limit for a component having a first peripheral part and a second peripheral part substantially opposite to the first peripheral part, the apparatus comprising: (a) a fixed grip for gripping the first peripheral part; (b) a micro-measurement system associated with the second peripheral part, the micro-measurement system including:

(i) a starter for initiating torsional oscillations in the component, (ii) a counter for counting the torsional oscillations, and (iii) a measurement device for measuring amplitudes of the torsional oscillations; and (c) a processor associated with the micro-measurement system for processing the torsional oscillation count and the measured amplitudes to determine a measure of damping as a function of amplitude.

According to a further feature of the present invention, there is also provided a heating system for substantially enclosing the component, the heating system maintaining the component within a given range of temperatures.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
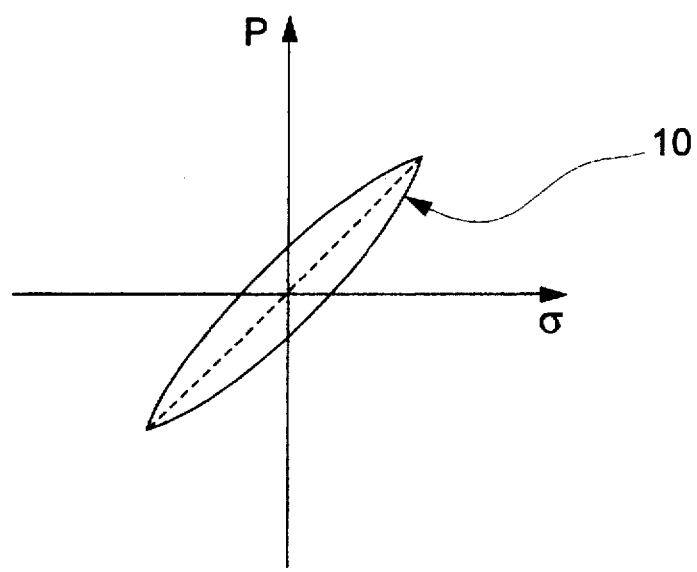
FIG. 1 is a schematic plot of deformation against stress for a sample undergoing reversed loading.

The present invention is of an apparatus and method for non-destructive determination a fatigue limit for a component.

The principles and operation of the apparatus and method according to the present invention may be better understood with reference to the drawings and the accompanying description.

Before addressing the details of the apparatus and method of the present invention, the principles underlying the present invention will be discussed briefly. It should be understood that any reference to physical properties and mechanisms related to the invention is given solely for the purpose of assisting the reader and should not in any way be considered to limit the scope of the invention.

In general terms, the apparatus and method of the present invention measure the stress-dependence of one or both of the micro-plastic deformation and the logarithmic damping of vibrations in a component. Certain features of this dependence are then identified as corresponding to critical values of stress from which a required fatigue limit is derived. Analysis of further features may additionally, or alternatively, provide information about fracture toughness of the component.

It is a particular feature of preferred embodiments of the present invention that the measurements taken relate to torsional or twisting deformation and vibration. The main types of static tests may be classified into tension, compression, bending and twisting tests. In tension tests, deformation results in a specimen becoming longer and thinner. In compression tests, deformation results in compression in which a specimen becomes shorter and thicker.

In bending tests, a biaxial stressed state is produced due to hindered lateral deformation. The lower part of a specimen becomes tensioned, and its upper part is compressed. In addition, the stresses which are dependent on the value of bending moment vary along the specimen length and cross-section. The maximum stresses are produced near the surface. All these factors complicate the estimation of average actual stresses and strains which are required for a rigorous characterization of the mechanical properties of a material.

In contrast, in twisting, the maximum tangential stresses exist in the planes perpendicular to the specimen axis while the maximum normal stresses are directed at an angle of 45°.

Study of the pattern of specimen failure in twisting tests is indicates that a single twist produces an identical stressed state over the entire length of a specimen from low stresses up to the instant of failure. One important consequence of the identical stressed state is that the gauge length and cross-section of the specimen remain constant during the test. Without in any way limiting the scope of the present invention, this is thought to be the reason that the twist measurements of the present invention provide a much more accurate estimation of the mechanical properties of a component than the above-mentioned methods.

The use of torsional measurements also enables the apparatus and method to be applied to real components of a wide range of shapes. In many cases, the geometry of complex components may preclude bending or tensile testing.

It should be appreciated that the method and apparatus of the present invention may be employed to advantage with components of a wide range of structural materials. Examples include, but are not limited to, metals and metal alloys, plastic and other polymer materials and wood. By way of example, reference will be made in the following description to physical mechanisms thought to be responsible for the certain observed properties in metal components. However, this should not be understood in any way as limiting the scope of the invention.

Referring now to the drawings, FIG. 1 shows a plot, generally designated 10, of deformation against stress for a sample undergoing reversed loading. It is well known that for flexible materials, even within the domain commonly described as elastic, the linear relationship of Hooke's Law between stress and deformation is imprecise. In a case of a specimen undergoing reversed loading, a hysterysis effect is observed as seen in plot 10. This hysterysis corresponds to energy loss due to heat generated within the specimen.

A quantitative measure of this energy loss for a given specimen may be deduced from the rate of damping of a torsion pendulum. Specifically, the measure of interest in the present context is the logarithmic damping $\delta$ defined as:

$$\delta = \ln(A_0/A_N)/N$$

where $A_0$ is the initial amplitude and $A_N$ is the amplitude of the Nth cycle. The initial amplitude $A_0$ may then be related back to applied stress $\sigma$ by subsequent calibration (i.e., construction of a stress-strain curve for the specimen).

Figure 2:
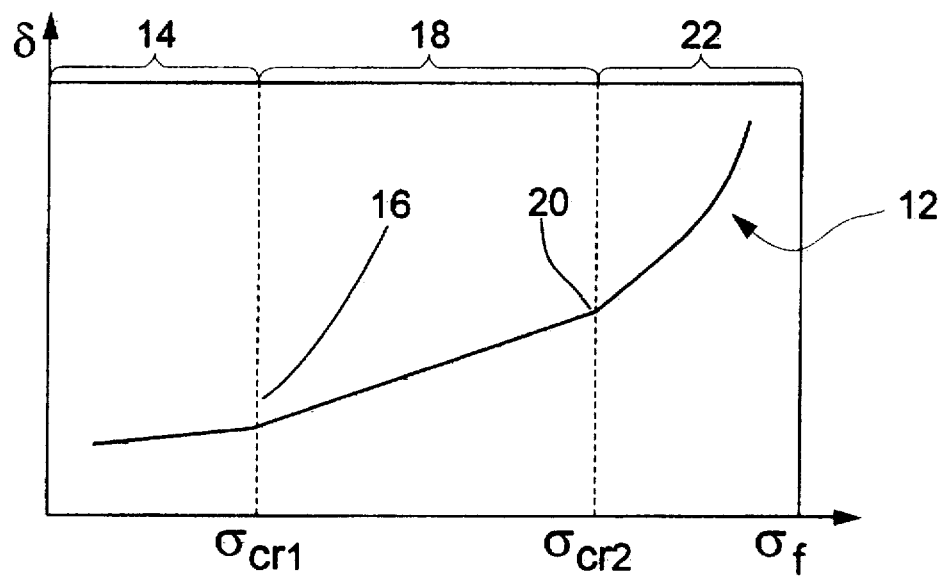
FIG. 2 is a schematic plot of variation in logarithmic damping as a function of repeated loading stress.

FIG. 2 shows a plot, generally designated 12, of logarithmic damping $\delta$ as a function of repeated loading stress $\sigma$. It will be noted that plot 12 may be subdivided into three regions. In a first region denoted 14, the logarithmic damping is effectively constant, i.e., substantially independent of the initial applied stress. At a first point of inflection, designated 16, the relationship changes to an approximately linear dependence which extends through a second region 18 up to a second point of inflection, designated 20. Above this point, a non-linear dependence is exhibited over a region designated 22.

Without in any way limiting the scope of the present invention, it is believed that these three regions correspond to different stages of mobility of dislocations. At low stress, dislocations are relatively unaffected by the deformation of the material. Above a first critical value of stress $\sigma_{cr1}$ corresponding to first point of inflection 16, deformation of the material causes displacements of dislocations within grains of the metal structure, giving rise to slip lines or bands within the individual grains. This gives rise to an increase in damping effect. At this stage, however, dislocations do not generally travel across grain boundaries. Above a second critical value of stress $\sigma_{cr2}$ corresponding to second point of inflection 20, dislocations start to spread across the grain boundaries, thereby giving rise to elongated slip bands and eventually cracks.

For these or other reasons, it has been found that the value of $\sigma_{cr2}$ may reliably be used as a measure of the fatigue limit for the material tested. In other words, this value corresponds to an amount of stress to which the material may be subjected through repeated or reversed loading without leading to fatigue failure.

Figure 3:
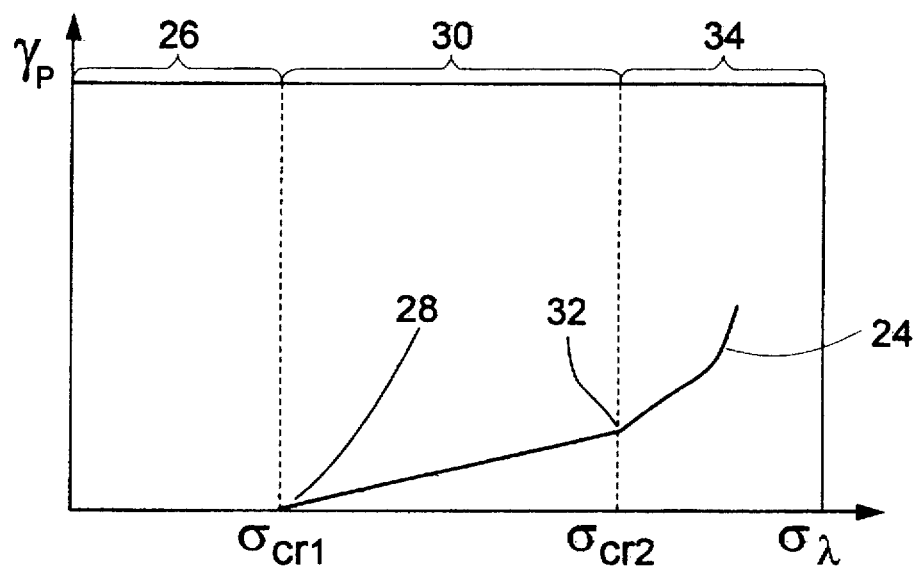
FIG. 3 is a schematic plot of variation in micro-plastic deformation as a function of repeated loading stress.

Turning now to FIG. 3, this shows a plot, generally designated 24, of micro-plastic deformation $\gamma_p$ as a function of repeated loading stress $\sigma$. The term micro-plasticity is used to refer to a phenomenon exhibited by a wide range of materials in which a temporary, generally elastic direct deformation results in a relatively small residual deformation after removal of the applied stress. The micro-plastic deformation may be conveniently defined as a proportion of the maximum direct deformation remaining after removal of the applied stress. For the purposes of the following description and claims, the term "micro-plastic" should be considered to refer to cases in which the residual deformation constitutes between about $10^{-7}$ and about $10^{-3}$ of the total direct deformation.

Plot 24 may be subdivided into three regions. In a first region denoted 26, the residual deformation is effectively zero. Above a first point of inflection, designated 28, applied stress results in a residual deformation which depends approximately linearly on the applied stress. This relationship extends through a second region 30 up to a second point of inflection, designated 32. Above this point, the residual deformation rises more rapidly within a region designated 34.

A comparison of FIGS. 2 and 3 reveals that the points of inflection 28 and 32 correspond to the same values of $\sigma_{cr1}$ and $\sigma_{cr2}$ as observed in plot 12. Without in any way limiting the scope of the present invention, it is reasonable to attribute the variation in residual deformation with applied stress to microscopic mechanisms similar to those described above.

Figure 4:
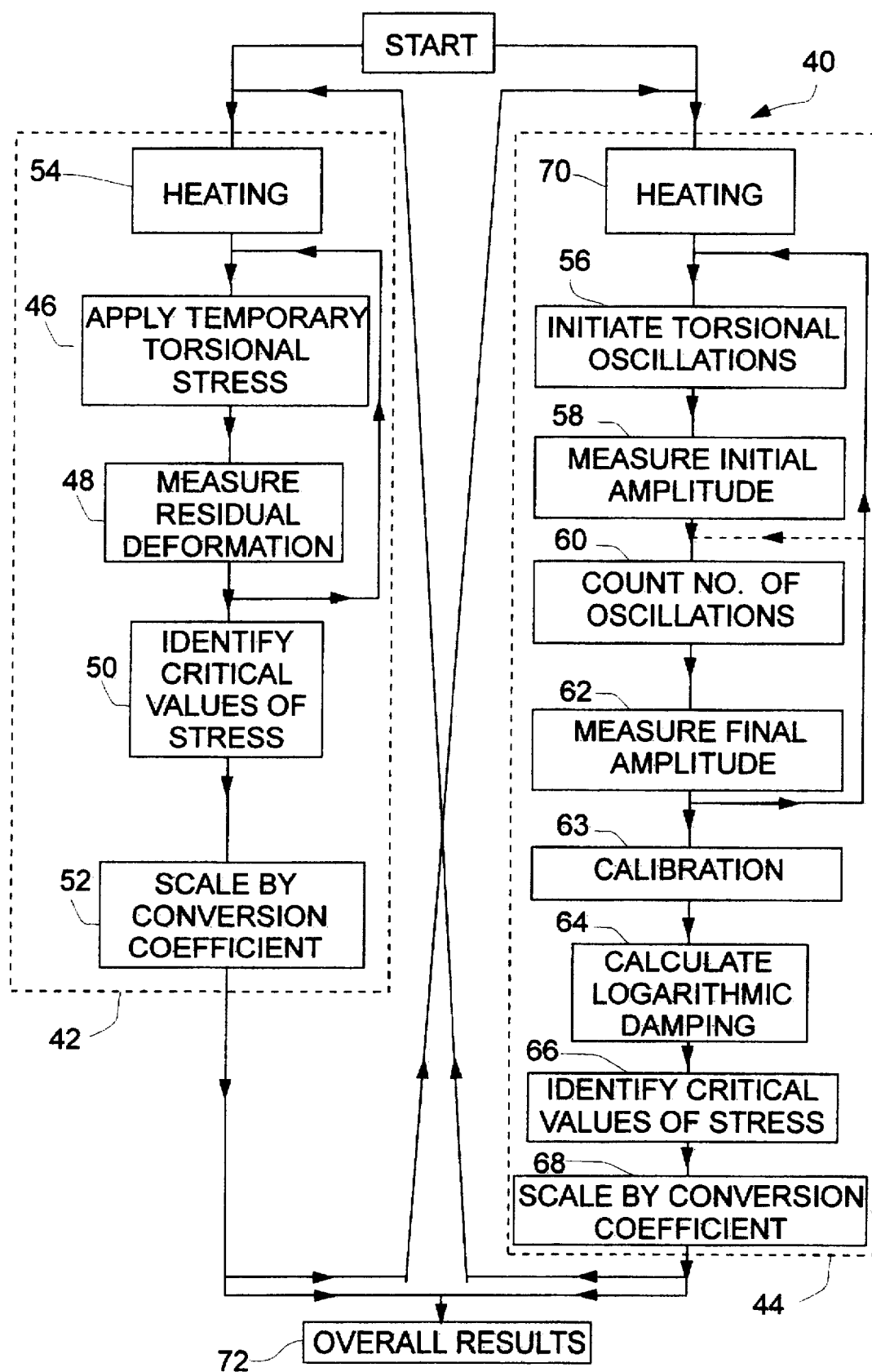
FIG. 4 is a block diagram of a method according to the present invention for measuring a fatigue limit for a component.

Turning now to FIG. 4, there is shown a method, generally designated 40, according to the teachings of the present invention, for determining a fatigue limit for a component. Method 40 preferably includes a micro-deformation sub-method 42 and an energy dissipation sub-method 44. It should be noted that sub-methods 42 and 44 may be performed sequentially in any order. If preferred, method 40 may be simplified to employ only one of the sub-methods. Specifically, in certain cases, the properties of the material being tested may preclude one of the sub-methods. However, the combination of the two sub-methods makes method 40 widely applicable to a great variety of components of a wide range of materials, as well as offering increased precision over either method used separately.

Relating first to the features of micro-deformation sub-method 42, this is performed by temporarily applying a known value of static loading stress to the component (step 46) and then, after release of the applied stress, measuring a resulting micro-plastic deformation in the component (step 48). These steps are repeated a plurality of times with different known values of stress of increasing magnitude so as to substantially determine the shape of a relationship between micro-plastic deformation and applied stress for values of stress below the yield point. At step 50, the measured values are processed, either graphically or numerically, to identify a critical value of stress corresponding to a change in the relationship between stress and micro-plastic deformation. Specifically, the critical value of interest is the value corresponding to $\sigma_{cr2}$ as defined in relation to FIG. 3 above.

It is important to note that correct identification of $\sigma_{cr2}$ is performed by identifying a point at which the nature of the stress-dependency of the micro-plastic deformation changes. This point may or may not coincide with an immediate increase in gradient. In certain cases, the critical value corresponds to a switch from linearity to non-linearity without a pronounced initial gradient change.

As mentioned earlier, it is a particular feature of a preferred method according to the present invention that the testing of the present invention is performed torsionally. In a case in which the fatigue limit of interest is the tensile or flexural fatigue limit, the critical value of $\sigma_{cr2}$ must additionally be scaled by a conversion coefficient (step 52). For a wide range of materials, it has been found that the conversion coefficient for converting a torsional fatigue limit to a flexural fatigue limit may be approximated by a value of 1.75 to an accuracy of ±5%. Exact values for each material may be evaluated once by conventional methods to construct a reference table of conversion coefficients. Conversion coefficients for generating tensile fatigue limits may be obtained in a similar manner.

Optionally, sub-method 42 may be employed to evaluate, or monitor changes in, a fatigue limit for a component under specific environmental conditions. By way of example, it may be useful to take measurements while a component is maintained at an elevated temperature which is approximately equal to the normal operating temperature of the component. For this purpose, a heating step 54 may be introduced prior to the taking of measurements. Typically, the heat is supplied continuously under thermostatic control throughout the taking of measurements.

In a similar manner, step 54 may be replaced by, or supplemented with, steps for applying other environmental conditions including, but not limited to, increased pressure, magnetic fields, longitudinal static loading and corrosive environments. In certain cases, measurements may be taken repeatedly over a period of exposure to the environmental conditions to monitor the affects of the conditions on the material properties.

Turning now to the features of energy dissipation sub-method 44, this includes a step 56 of initiating torsional oscillations in the component. The oscillations are preferably of low frequency such as, for example, between about 1 and 100 Hz. The required frequency may be obtained by loading the free end of the component with a body of suitable moment of inertia. A measurement is then made (step 58) of an initial angular amplitude of oscillation, $A_0$. Immediately after measurement 58, a number n of oscillations of the component are counted in step 60. Then, in step 62, a final angular amplitude of oscillation, $A_n$ at the end of n oscillations is measured. Steps 58, 60 and 62 are then repeated a number of times so as to measure pairs of $A_0$ and $A_n$ for different initial angular amplitudes. Sufficient measurements are made to substantially span the range of values of stress below the yield point.

In certain cases, it may be possible to repeat only steps 60 and 62, or alternatively steps 58, 60 and 62. Typically, however, step 56 is also repeated between each set of measurements.

At some stage of sub-method 44, and typically after completion of steps 58–62, a calibration step 63 is performed. Calibration step 63 is performed by applying a range of values of static stress to the component and measuring the corresponding direct deformations. This information allows each initial amplitude $A_0$ to be associated with a specific value of applied stress.

For each set of measurements, a measure of damping corresponding to the initial angular amplitude $A_0$ is calculated (step 64). The measure used is preferably the logarithmic damping $\delta$, as defined above. It is immaterial whether calculation step 64 is performed repeatedly between sets of measurements, concurrently with the measurement process, or after completion of all the measurements.

Then, at step 66, the measured values are processed, either graphically or numerically, to identify a critical value of stress corresponding to a change in the relationship between stress and logarithmic damping. Specifically, the critical value of interest is the value corresponding to $\sigma_{cr2}$ as defined in relation to FIG. 2 above.

As with sub-method 42, sub-method 44 may also include a step 68 of scaling $\sigma_{cr2}$ by a conversion coefficient. Specifically, since the testing of the present invention is preferably performed torsionally, a torsional-to-tensile or torsional-to-flexural conversion coefficient is generally required, as described above in the context of sub-method 42.

Sub-method 44 may also employ a step of applying environmental conditions likely to affect the fatigue limit of the component, as was described above in the context of sub-method 42. This possibility is represented, by way of example, by heating step 70, analogous to step 52, prior to the taking of measurements.

As mentioned earlier, and as indicated by the flow arrows of FIG. 4, method 40 may perform sub-methods 42 and 44 in either order, or individually. In the case that both sub-methods are employed, the results are combined at step 72 to generate an overall result of increased accuracy.

It is a particular feature of both sub-methods that testing is performed at stresses below the yield point of the material concerned such that the testing does not affect the properties of the material. In this sense, method 40 is described as a non-destructive method.

Figure 5:
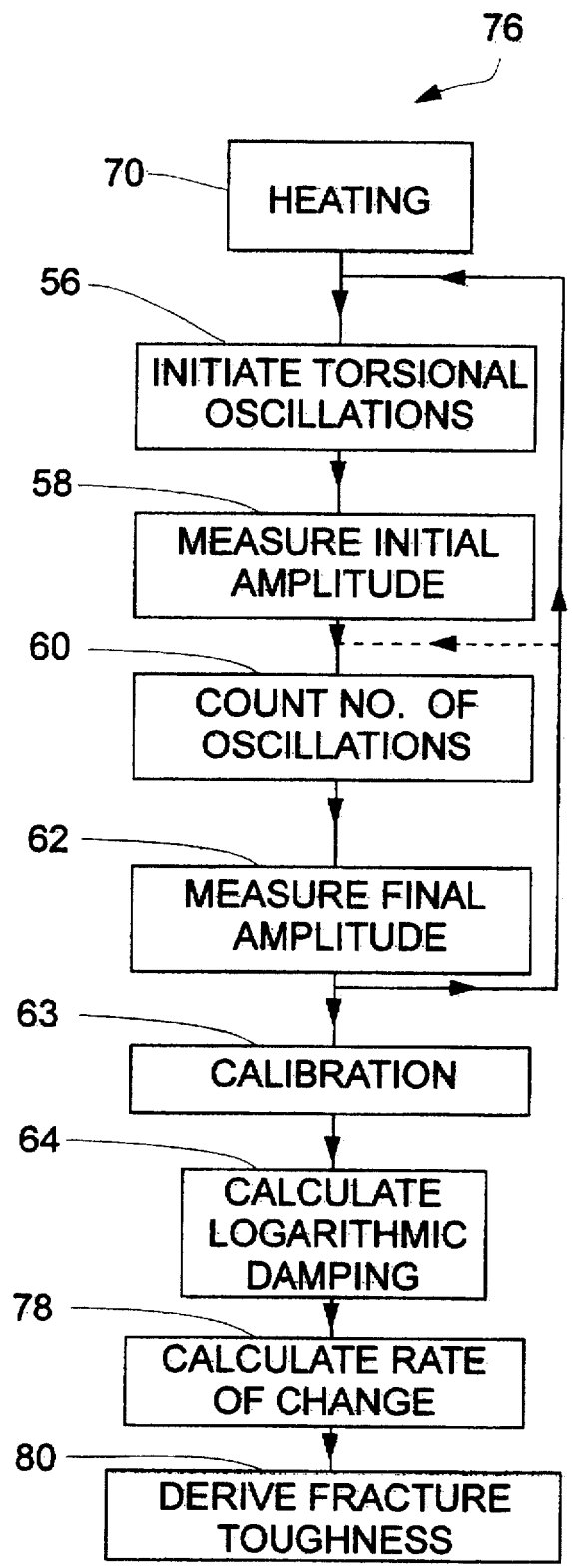
FIG. 5 is a block diagram of a method according to the present invention for deriving information relating to fracture toughness for a component.

Turning now to FIG. 5, this shows a method, generally designated 76, operative according to the present invention, for non-destructive derivation of fracture toughness or changes therein for a component. Generally speaking, method 76 is similar to sub-method 44 above. Equivalent elements are labelled similarly. After step 64, method 76 includes a step 78 of calculating a rate of change of in the relationship between applied stress and logarithmic damping. Specifically, the rate of change of interest is the gradient of second region 18 of FIG. 2. In step 80, this rate of change forms the basis for the calculation of a value of fracture toughness, or alternatively, a proportional change in the fracture toughness of the material of the component.

More specifically, it is known that fracture toughness is quantified by three stress intensity coefficients $K_I$, $K_{II}$ and $K_{III}$, defined in relation to the relative directions of the crack surfaces and the applied stress. The coefficient of most structural importance is $K_I$ for which the applied stress tends to directly open the crack.

It may be demonstrated that $$K_I = \sigma_{cr2} \sqrt{(\alpha_1/\alpha_2)}$$

wherein $\alpha_1$ is the tangent of the gradient between $\sigma_{cr1}$ and $\sigma_{cr2}$, and $\alpha_2$ is the tangent of the gradient immediately above $\sigma_{cr2}$. It follows that measurements of changes in the gradient of the lines between $\sigma_{cr1}$ and $\sigma_{cr2}$, or immediately above $\sigma_{cr2}$, may be used to estimate changes in the fracture toughness. Precise measurements of each of these values may also be employed to evaluate an actual value of the fracture toughness.

Turning now to the apparatus of the present invention, this will be described with reference to FIG. 6. It will be understood that the methods of the present invention may be implemented using a wide range of apparatus designs, and with varying degrees of automation. It should be appreciated that a separate apparatus may be employed for performing each of sub-methods 42 and 44. However, in a preferred embodiment, a single apparatus is provided for performing both sub-methods sequentially.

Figure 6:
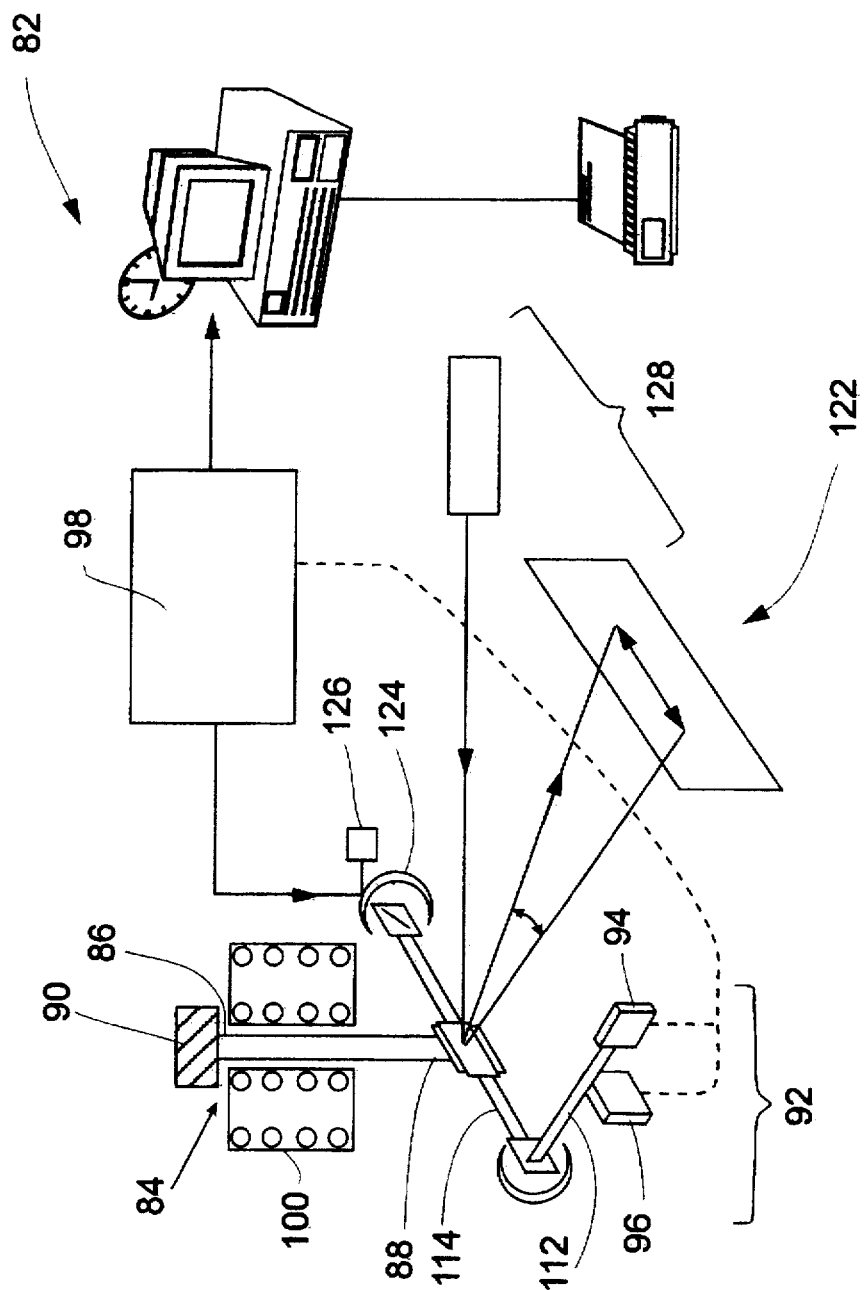
FIG. 6 is a schematic perspective view of an apparatus, constructed and operative according to the teachings of the present invention, for measuring a fatigue limit for a component.

Referring now to FIG. 6, this shows an example of apparatus, generally designated 82, constructed and operative according to the teachings of the present invention, for non-destructive determination of a fatigue limit for a component 84 which has a first peripheral part 86 and a second peripheral part 88 substantially opposite to first peripheral part 86. Generally speaking, apparatus 82 includes a fixed grip 90 for gripping first peripheral part 86 and a first micro-measurement system 92 attached to second peripheral part 88. First micro-measurement system 92 features a torque loading device 94 for applying different values of torque to the component between first and second peripheral parts 86, 88. The torque is applied and released slowly, typically over a period of about one second each. A measurement device 96 is provided for making precise measurements of residual angular micro-plastic deformation corresponding to each of the different values of torque applied to component 84. Apparatus 82 also includes a processor 98 for processing the values of torque and the corresponding angular micro-plastic deformations to identify a critical value of torque corresponding to a change in the relationship between torque and micro-plastic angular deformation. Processor 98 is associated with various conventional input and output interfaces which are indicated here schematically. The above features enable apparatus 82 to be used to implement sub-method 42 in a manner which will be fully understood by reference to the description above.

Optionally, apparatus 82 also features a heating system 100 substantially enclosing component 84 for maintaining the component within a given range of temperatures Heating system 100 may be replaced by, or supplemented with, other apparatus for providing specific environmental conditions around the component during testing. The details of any such apparatus will be fully understood by one ordinarily skilled in the art from the examples in the description of the method of the present invention given above.

In order to allow apparatus 82 to be used also for implementing sub-method 44, a removable link 112 is preferably provided between first micro-measurement system 92 and second peripheral part 88 to which it is attached.

Disconnection of removable link 112 allows apparatus 82 to be used for the low-frequency oscillatory testing of the energy-loss sub-method. Other features required specifically for performance of sub-method 44 include a second micro-measurement system 122 attached to second peripheral part 88. Second micro-measurement system 122 features a starter 124 for initiating torsional oscillations in component 84, a counter 126 for counting the torsional oscillations, and a measurement device 128 for measuring amplitudes of the torsional oscillations. Measurement device 128 is typically an optical reflection-type device, as illustrated here schematically. The desired low frequency of oscillation, typically between about 1 and 100 Hz., may be set by selection of a torsion pendulum-type cross-bar 114 of appropriate moment of inertia. Processor 98 is also associated with second micro-measurement system 122 for processing the torsional oscillation count and the measured amplitudes to determine a measure of damping as a function of amplitude. The use of apparatus 82 for implementing sub-method 44 may be understood fully by reference to the description of sub-method 44 above. Removable link 112 is disconnected during performance of oscillatory measurements, and is reconnected for calibration step 63.

It will be appreciated that the above descriptions are intended only to serve as examples, and that many other embodiments are possible within the spirit and the scope of the present invention.

What is claimed is:

1. A non-destructive method of determining a flexural fatigue limit for a component, the method comprising the steps of:
   (a) measuring a micro-plastic deformation corresponding to each of a plurality of different known values of torsional stress applied to the component;
   (b) identifying a critical value of stress corresponding to a change in the relationship between stress and micro-plastic deformation; and
   (c) multiplying said critical value of stress by a torsional-to-flexural conversion coefficient.

2. A method as in claim 1, further comprising the steps of:
   (a) initiating torsional oscillations in the component;
   (b) measuring an initial angular amplitude of oscillation, $A_0$;
   (c) counting a number, n, of oscillations after measurement of said initial angular amplitude;
   (d) measuring a final angular amplitude of oscillation, $A_n$ at the end of said number, n, of oscillations;
   (e) repeating at least steps (c) and (d) a plurality of times for different initial angular amplitudes to obtain a plurality of pairs of measurements $A_0$, $A_n$;
   (f) for each of said pairs of measurements, calculating a measure of damping corresponding to said initial angular amplitude; and
   (g) identifying a critical value of initial angular amplitude corresponding to a change in the relationship between amplitude and damping.

3. A non-destructive method of determining a fatigue limit for a component, the method comprising the steps of:
   (a) initiating torsional oscillations in the component;
   (b) measuring an initial angular amplitude of oscillation, $A_0$;
   (c) counting a number, n, of oscillations after measurement of said initial angular amplitude;
   (d) measuring a final angular amplitude of oscillation, $A_n$ at the end of said number, n, of oscillations;

(e) repeating at least steps (c) and (d) a plurality of times for different initial angular amplitudes to obtain a plurality of pairs of measurements $A_0$, $A_n$;

(f) for each of said pairs of measurements, calculating a measure of damping corresponding to said initial angular amplitude; and (g) identifying a critical value of initial angular amplitude corresponding to a change in the relationship between amplitude and damping.

4. A method as in claim 3, wherein said oscillations are at a frequency of between about 1 and 100 Hz.

5. A method as in claim 3, wherein the fatigue limit of interest is the flexural fatigue limit, the method further comprising a step of multiplying said critical value of stress by a torsional-to-flexural conversion coefficient.

6. A method as in claim 3, further comprising a step of applying to the component an environmental condition likely to affect the fatigue limit during making of said measurements.

7. A method as in claim 6, wherein said environmental condition includes exposure to an elevated temperature.

8. A method as in claim 3, further comprising the steps of:

(a) measuring a micro-plastic deformation corresponding to each of a plurality of different known values of stress applied to the component; and (b) identifying a critical value of stress corresponding to a change in the relationship between stress and micro-plastic deformation.

9. A non-destructive method of deriving information relating to fracture toughness for a component, the method comprising the steps of:

(a) initiating torsional oscillations in the component;

(b) measuring an initial angular amplitude of oscillation, $A_0$;

(c) counting a number, n, of oscillations after measurement of said initial angular amplitude;

(d) measuring a final angular amplitude of oscillation, $A_n$ at the end of said number, n, of oscillations;

(e) repeating at least steps (c) and (d) a plurality of times for different initial angular amplitudes to obtain a plurality of pairs of measurements $A_0$, $A_n$;

(f) for each of said pairs of measurements, calculating a measure of damping corresponding to said initial angular amplitude; and (g) calculating at least one rate of change in the relationship between amplitude and damping.

10. A method as in claim 9, further comprising a step of identifying first and second critical points corresponding to changes in the relationship between amplitude and damping, and wherein one of said rates of change is calculated from measurements falling between said first and second critical points.

11. A method as in claim 1, further comprising a step of applying to the component an environmental condition likely to affect the fatigue limit during said step of measuring.

12. A method as in claim 11, wherein said environmental condition includes exposure to an elevated temperature.

* * * * *